United States Patent [19]

Sato et al.

[11] 4,405,467
[45] Sep. 20, 1983

[54] SUBLIMABLE COMPOSITIONS AND PROCESS FOR PRODUCING MOLDINGS

[75] Inventors: Haruhito Sato; Hiroshi Ichikawa; Hiroshi Hayashi; Konomu Kurisaki, all of Sodegaura, Japan

[73] Assignee: Idemitsu Kosan Company Limited, Tokyo, Japan

[21] Appl. No.: 288,410

[22] Filed: Jul. 30, 1981

Related U.S. Application Data

[62] Division of Ser. No. 862,624, Dec. 20, 1977, Pat. No. 4,301,043.

[30] Foreign Application Priority Data

Dec. 25, 1976 [JP] Japan .................................. 51-155651
Dec. 25, 1976 [JP] Japan .................................. 51-155653
May 21, 1977 [JP] Japan .................................. 52-58220
May 24, 1977 [JP] Japan .................................. 52-59359
Jun. 7, 1977 [JP] Japan .................................. 52-66298
Oct. 17, 1977 [JP] Japan .................................. 52-123460

[51] Int. Cl.$^3$ ...................... C09K 3/00; A61K 7/46
[52] U.S. Cl. ........................................ 252/1; 239/60; 252/384; 252/399; 252/407; 252/522 A; 424/19; 424/356; 424/DIG. 10

[58] Field of Search .................. 252/1, 384, 399, 407, 252/522 A; 239/60; 424/356, DIG. 10; 585/352

[56] References Cited

U.S. PATENT DOCUMENTS

1,685,624  9/1928  Andrews ............................. 260/706
3,128,316  4/1964  Schneider ........................... 585/352
3,418,387  12/1968  Aala et al. .......................... 585/352
3,781,428  12/1973  Hennart et al. ................... 239/60 X

FOREIGN PATENT DOCUMENTS

142902  5/1920  United Kingdom ................ 260/706

Primary Examiner—Leland A. Sebastian
Attorney, Agent, or Firm—Frishauf, Holtz, Goodman & Woodward

[57] ABSTRACT

A sublimable composition comprising adamantane and a sublimable hydrocarbon other than adamantane. This composition is quite useful as a carrier for a mothproofing agent, a perfume, and the like. From this composition can be produced a molded product by melt molding, for example.

11 Claims, 9 Drawing Figures

SUBLIMABLE COMPOSITIONS AND PROCESS FOR PRODUCING MOLDINGS

This is a division of application Ser. No. 862,624 filed Dec. 20. 1977, now U.S. Pat. No. 4,301,043.

BACKGROUND OF THE INVENTION

1. Field of the Invention

This invention relates to sublimable compositions. More particularly it is concerned with sublimable compositions comprising adamantane and other sublimable hydrocarbons and if necessary, containing effective components and antioxidants. Also, it is concerned with process for producing molded product from the above sublimable compositions, and sublimable multi-layer molded product.

2. Description of the Prior Art

As supporters or carriers for retaining effective components such as perfume, moth-proofing agent and the like, there have hitherto been known non-volatile supporters such as agar gel, polyacrylamide and the like or sublimable carriers, etc.

With the non-volatile supporters, however, it is difficult to retain the effective components for a long period of time because the effective components evaporate as the supporters themselves are air-dried. Furthermore, the non-volatile supporters have the disadvantage in that water comes out or oozes from a molded product formed thereof. As examples of sublimable carriers widely used, camphor, naphthalene, p-dichlorobenzene, and the like can be listed. These sublimable carriers, however, have their specific odors providing a irritating and unpleasant feeling. Moreover, it is difficult to provide the sublimable carriers with the desired aroma.

Adamantane is also sublimable, non-toxic, chemically stable and water-insoluble, and it is thus known as a sublimable carrier. A carrier formed of adamantane alone, however, has the disadvantages in that the effective components contained therein volatilize more rapidly than admantane sublimates, and they are consumed in a short period of time, and in that it is not possible to mold the carrier by a melt molding process.

SUMMARY OF THE INVENTION

The principal object of this invention is to provide a sublimable composition from which it is possible to produce a carrier capable of containing a large amount of effective components such as perfume, moth-proofing agent and the like, and capable of retaining them for a long period of time, and having a sufficient strength corresponding to the use thereof.

It has now been found that the above object is attained by combining adamantane and one or more sublimable hydrocarbons such as endo-trimethylenenorbornane (hereinafter referred to as TMN), cyclododecane (hereinafter referred to as CD), and the like.

Other objects and advantages of this invention will become apparent from the following detailed explanation.

Thus this invention provides a sublimable composition comprising adamantane and a sublimable hydrocarbon other than adamantane. Also, this invention is concerned with a process for producing a molded product from the sublimable composition, and a sublimable multi-layer molded product formed of the sublimable composition.

DETAILED DESCRIPTION OF THE INVENTION

Adamantane is a non-toxic and odorless sublimable substance, and a molding, i.e. a molded product, formed of adamantane has a good shape retention property and a high mechanical strength. Moreover, its crystal particles can retain effective components such as liquid perfume and the like in a relatively large amount in the space therebetween. In addition, since adamantane has a high melting point (m.p. 263° C.), it is free from the sudden depression in melting point which is usually encountered in mixing two or more kinds of crystalline hydrocarbons. Thus adamantane can easily be blended with other sublimable hydrocarbons.

Sublimable hydrocarbons which can be used in combination with adamantane in this invention, include TMN, CD, norbornane, trimethylnorbornane, naphthalene and the like. In preparing a composition of this invention, one or more compounds are selected appropriately from the above sublimable hydrocarbons and mixed with adamantane. Among these sublimable hydrocarbons, TMN and CD are preferably used.

The ratio of adamantane and a sublimable hydrocarbon other than adamantane is not especially limited and can be appropriately determined according to the properties of the sublimable hydrocarbon used. In general, the composition of this invention comprises 10 to 50% by weight of adamantane and 90 to 50% by weight of a sublimable hydrocarbon other than adamantane.

TMN is a quite excellent sublimable hydrocarbon for use in combination with adamantane according to this invention. TMN is a non-toxic and sublimable hydrocarbon like adamantane, and it is in the form of wax-like crystals having caking properties at room temperature. The shape retention property after molding of TMN is not good although it has excellent moldability and releasability. Therefore, if it is allowed to stand in the air at room temperature, it is subject to natural deformation. Moreover, if TMN is used singly, it cannot contain a large amount of effective components such as perfume and the like.

When adamantane and TMN are blended in appropriate proportions, the defects of each components are covered by the other. Thus, this composition obtained provides molded products having high abilities to contain and retain a large amount of effective components such as perfume and the like, and having high mechanical strength. A composition comprising 1 to 60% by weight of adamantane and 99 to 40% by weight of TMN is considered suitable for practical use. In particular, a range of 10 to 25% by weight of adamantane and 90 to 75% by weight of TMN is preferred for maintaining an adequate balance between the ability to contain and retain effective components such as perfume, moth-proofing agents and the like, and the mechanical strength. In a composition of adamantane and TMN prepared by mixing them within the above range, since the amount of adamantane added is small, and since the sublimation rate of adamantane is lower than that of TMN, the adamantane sublimates keeping a balance with TMN and the whole shape (size) of the molding prepared with the composition gradually decreases until it disappears. During use, neither adamantane nor TMN is singly left in the composition. Thus, the composition acts as an excellent carrier, which is defined as that part of the composition excluding the effective components, for effective components until it is completely sublimated.

Composition prepared in a range of 1 to 10% by weight of adamantane and 99 to 90% by weight of TMN is markedly improved in the ability to contain and retain the effective components through the action of a small amount of adamantane is compared with a composition in which no adamantane is used: i.e., TMN is used alone, although its shape retention properties after molding are somewhat inferior.

On the other hand, in composition comprising 25 to 60% by weight of adamantane and 75 to 40% by weight of TMN, adamantane particles form an appropriate three dimensional network structure in which the particles are combined together continuously, and the spaces of the network structure are filled with TMN. When this composition is sublimated, adamantane is left on the surface thereof owing to the difference between the sublimation rates of adamantane and TMN, resulting in the formation of a network layer of adamantane. This layer is brittle and can be easily removed by flowing water thereon. When a molding formed of the composition is reduced in size and a network of adamantane is formed thereon, since there are many spaces in the network and the strength of the network is weak, the network collapses forming finely divided particles.

CD is also excellent as a sublimable hydrocarbon used in combination with adamantane in this invention. CD is a non-toxic, sublimable hydrocarbon like adamantane. Although a molding formed of CD has a relatively high mechanical strength, it is free from the powder-coating thereon since its melting point is low (61° C.). The molding formed of CD alone can contain almost no effective components such as perfume and the like.

The combined use of adamantane and CD in an appropriate ratio, however, forms composition from which it is possible to produce molded products having a high ability to contain and retain the effective components, free from the powder-coating, and having very high mechanical strength. When the amount of adamantane added is larger, CD covers thinly the surface of solid crystal particles of adamantane, resulting in the formation of a three-dimensionally continuous structure of CD. Therefore, the effective components are contained in the spaces between adamantane particles covered with CD and prevented from volatilizing. As a result, the retention characteristics of the effective components are increased.

In a composition comprising adamantane and CD in accordance with this invention, the ratio of adamantane to CD is not especially limited. When the content of the effective components is especially required to be increased, the both components are mixed so that the ratio is 10 to 90% by weight of adamantane and 90 to 10% by weight of CD. Where it is necessary to retain the effective components particularly for a long period of time, they are mixed so that the ratio is 50 to 95% by weight of adamantane and 50 to 5% by weight of CD. Furthermore, where it is especially required to form a molding having a high mechanical strength, it is effective to mix them in a ratio of 20 to 95% by weight of adamantane and 80 to 5% by weight of CD. Therefore, for generally improving the properties of the composition, it is preferred to mix them in such a manner that the ratio is 50 to 90% by weight of adamantane and 50 to 10% by weight of CD. Where heat-deterioration of the effective components is prevented and the composition is subjected to a melt-molding, 10 to 50% by weight of adamantane and 90 to 50% by weight of CD are preferably blended in order to decrease the temperature initiating the crystallization of the composition. In addition, the sublimation rate of the composition can be easily controlled by changing the ratio of adamantane to CD.

A sublimable composition comprising adamantane and one or more sublimable hydrocarbon other than adamantane according to this invention has excellent properties as a sublimable carrier for various kinds of effective components.

Various effective, that is, active, components can be added to the sublimable composition of this invention. For example, perfume and those materials having moth-proofing, insect-repelling, insect-attracting, deodorizing, insect-killing, preservative, mold-proofing, and rust-preventive abilities, etc., can be employed.

Perfumes and deodorizing materials which can be used in this invention, include synthetic perfumes, for example, terpene based perfumes such as α-ionone, borneol, camphor, linalool, geraniol, citronellol, citronellal, citral, linalyl acetate, terpineol and the like; aromatic perfumes such as cumarin, nerolin, diphenyloxide, β-phenetylalcohol, acetophenone, benzylalcohol and the like; aliphatic perfumes such as alcohol, aldehyde, lactone and the like; etc., animal perfumes such as musk, ambergris, and the like, and vegetable perfumes such as peppermint oil, lavendor oil and the like. It is most preferred that crystalline perfumes are used singly. Liquid perfumes may be used. In general, crystalline and liquid perfumes are used in combination with each other. The amount of perfume added is generally sufficient to be below 10% by weight. Within this range, it is not necessary to change the above described composition ratio.

As moth-proofing and insect-repelling agents, for example, for the purpose of repelling mosquitos, phenetyl-alcohol, cineol, cinnanic alcohol and the like can be used. For moth-proofing against clothes, e.g. against the moth which is famous as a harmful insect for wool, linalool, linalooloxide, l-menthol, thymol, and the like can be used. In addition, insectirepellent agents such as cinnamic aldehyde, citronellol, diethyltoluamide, dibutyl phthalate and the like can be used. The amount of the moth-proofing or insect-repelling agent added is generally 0.01 to 20% by weight of the composition. In adding these moth-proofing agents and the like, if necessary, perfume and other materials can be appropriately added in combination therewith.

As insecticides, O,O-dimethyl-O-(2,2-dichlorovinyl)-phosphate and the like can be used. As preservative, butyl p-hydroxybenzoate and the like can be used. In addition, as rust-preventive, morpholine, dicyclohexylamine, diisopropylamine and the like can be used, and as mold-proofing agents ethyl pyrocarbonate, β-propiolactone and the like.

It is preferred that volatile effective components are added to a composition of adamantane and TMN and that those effective components which are not readily volatilized, are added to a composition of adamantane and CD.

The effective components as described above which are added to the composition of this invention, generally include easily oxidizable materials such as aldehydes, nitrogen-containing compounds, double bond-containing compounds and the like. Therefore, antioxidants can be added in combination with the effective components in order to maintain the activity of the effective components for a long period of time.

The term "antioxidant" used herein indicates organic compounds having the ability to prevent or control the action of oxygen against materials suffering from auto-oxidization under the conditions of light, heat and the like. These antioxidants include polymerization inhibitors and polymerization retarders. They are classified into radical chain stoppers, peroxide decomposers and metal deactivators according to the action mechanism thereof. They include quinones, aromatic amines, aldehydeamines, phenols and the like. It is preferred that antioxidants used in this invention have strong oxidation preventing abilities, do not lose their volatility when themselves oxidized, and are little colored. In more detail, hydroquinone monomethyl ether, hydroquinone, resorcin and the like are preferred. In addition, dibutyloxy toluene, butyloxy anisol, isoamyl gallate, phenylnaphtylamine, BHT (2,6-di-tert-butyl-p-cresol), β-naphthol, sesamol, quercetin and the like can be used.

While the amount of antioxidants added is not especially limited, they are usually added in amounts of 0.01 to 10% by weight based upon the weight of effective components.

The compositions which contain an antioxidant is incorporated are free from degeneration, polymerization and the like of the effective components used during the use thereof. Thus all of the effective components are efficiently used, and there is no residue of degenerated materials and polymerized materials.

The composition of this invention can be molded by any procedure. For example, adamantane and one sublimable hydrocarbon are mixed in an appropriate ratio, melted by heating, uniformly mixed. To this molten mixture is added, if necessary, effective components and antioxidants. The resulting mixture is solidified by cooling, pulverized and then compression-molded into a desired form.

In a molding obtained by the above compression-molding, the effective components, adamantane and the like are uniformly distributed, the surface strength is not sufficient, and it is not possible to prevent the effective components from oozing out of the surface during the compression. On the other hand, if melt molding is employed, adamantane is distributed on the surface of a molding in a high concentration, resulting in a marked increase in the surface strength of the molding. Furthermore, the effects can be obtained that releasability, dimentional stability and the like are increased and that the surface of the molding is well finished. In addition, the advantages can be obtained in that the additives are prevented from oozing and that the additives are stored in the core portion of the molding in a high concentration. Moreover, the shape retention property of the molding after molding is good. Although the melt-molding can be carried out by conventional procedures, the molding temperature is preferably 10° to 20° C. higher than a temperature initiating the crystallization of the molten mixture.

Incorporation of adamantane increases the crystallization rate of a composition. Thus the time required for solidifying a molten composition is shortened and molding speed is increased.

Hereinafter, a sublimable multi-layer molding prepared by overlaying a plurality of layers formed of compositions having different contents of effective components so that the volatility ratio of the effective components be always maintained at a constant level, will be explained.

This sublimable multi-layer molding comprises adamantane, a sublimable hydrocarbon other than adamantane and an effective component, which is characterized in that the content of effective component contained in each layer is gradually increased from the surface layer toward the inside or lower layer. The required amount of effective component to be incorporated in each layer should be controlled so that the volatility ratio of the effective component is always maintained at a constant level during the sublimation of the molding. In general, the volatility ratio of the effective component suffers a sudden decrease after the starting of sublimation. Therefore, the effective component content of each layer is required to be gradually increased.

The proportion at which the effective component content is gradually increased from the surface layer toward the inside or lower layer, cannot be determined unconditionally because it varies according to the kind of sublimable hydrocarbon, the kind of effective component, the thickness of each layer, the form of molding, the sublimation circumstances and the like. For example, in the case of an adamantane-TMN based sublimable multi-layer molding comprising layers of the same thickness, it is preferred that the ratio of the effective components contained in two layer adjacent to each other is 1:2 to 10.

Figure 7:
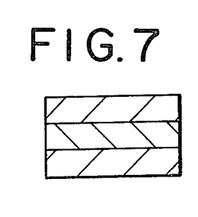
FIGS. 7 and 8 are sectional views of embodiments of a multi-layer molding according to this invention.

The shape and the structure of the multi-layer molding of this invention are not especially limited. In general, the multi-layer molding is classified into the following two types:

In the first type, plate-like layers (disk layers, plate layers and the like) are overlaid one upon another as shown in FIG. 7. In this kind of molding, it is preferred that only the surface of the most upper layer is exposed to the atmosphere and all of the other layers are shielded from the atmosphere by wrapping, for example. In this case, if the effective component content is successively increased from an upper layer toward a lower layer, taking an variation between the sublimation rate of an initial layer and a present one into consideration, the upper layer is first consumed and lower layers are successively exposed to the atmosphere. Thus it is possible to always keep the volatility ratio of the effective component at a constant level.

Figure 8:
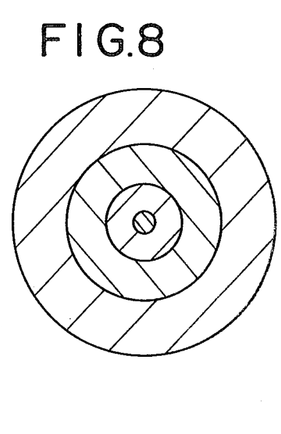

The second type of molding is in the spherical form as shown in FIG. 8, in which an outer layer is laminated on a inner layer in such a manner that the former envelopes the latter. In this case, if the effective component content is gradually increased from an outer layer toward an inner layer, it is possible to maintain the volatility ratio of the effective component at a constant level during the sublimation of the molding.

Either of the above two types can be preferably used for the multi-layer molding of this invention. However, the first type of molding as shown in FIG. 7 wherein plate-like layers are overlaid one upon another, is economically advantageous from the standpoint of production.

As the number of layers constituting the molding increases, it is more preferred. It is ideal that innumerable layer are formed and the effective component content in the layers are changed continuously and gradually. However, as the number of the layers constituting the molding increases, the production steps are more complicated, which is not practical.

In a two-layer type of adamantane and TMN carrier, for example, the ratio of the effective component in the upper layer and the lower layer 1:4.

The multi-layer molding of this invention can be formed by various procedures. For example, in the case of the first type of molding in which plate-like layers are overlaid one upon another, a suitable sublimable carrier and an effective component are first selected and melted by heating, and then the resulting molten mixture is cooled and molded into a layer. This layer is placed in a mold. Thereafter, the sublimable composition containing the effective component in a lower concentration than that of the first layer is prepared, melted by heating and poured upon the first layer previously placed in the mold to form a second layer. By repeating this procedure, a multi-layer molding of this invention in which the effective component content is successively increased from an upper layer to a lower layer, can be obtained.

With the multi-layer molding of this invention, it is possible to maintain the volatility ratio of the effective component at a materially constant level always during the use thereof. Therefore, the effect of the effective component is exhibited uniformly for a long period of time.

The following examples and comparative examples are given to illustrate embodiments of this invention. It will be understood that these examples are illustrative, and this invention is not to be considered as restricted thereto except as indicated in the appended claims.

EXAMPLE 1

A mixture of adamantane and TMN was melted and uniformly mixed. After cooling, this molten mixture was compression molded to form a disk-like sublimable molding of a diameter of 10 cm, a height of 0.5 cm and a weight of 40 g. This molding was placed in an open box formed of polyacrylonitrile and dipped in 10 liters of water therein. The upper layer of the water was stirred at a speed of 30 revolutions per minute for 10 minutes with an agitator provided with agitating blades of 8 cm to thereby wash the surface of the disk-like molding. After the processing of water-washing, the disk-like molding was air-dried at room temperature and sublimated. This procedure was repeated at 3 hour intervals.

The sublimation rate of the molding gradually decreased at the beginning, but it became constant after several days. The value at which the sublimation rate was constant, is indicated as a relative sublimation rate relative to adamantane in Table 1.

For comparison, the molding was not washed with water and sublimated in the air. The relative sublimation rate obtained is also shown in Table 1.

If the TMN content is below 40% by weight, where the molding is washed with water, a ratio at which the sublimation rate increases, is small and the sublimation rate is insufficiently controlled.

TABLE 1

| | TMN Content (% by weight) | Relative Sublimation Rate |
|---|---|---|
| Sublimation in the air[*1] | 0 | 1 |
| | 20 | 1.4 |
| | 40 | 2.1 |
| | 60 | 2.9 |
| Sublimation after water-washing[*2] | 0 | 1 |
| | 20 | 1.15 |
| | 40 | 1.5 |
| | 60 | 2.2 |

[*1]Only in the case of adamantane: 0.011 g/cm² · day
[*2]Only in the case of adamantane: 0.012 g/cm² · day

EXAMPLE 2

A mixture of 30% by weight of adamantane and 70% by weight of TMN was melted and uniformly mixed. After cooling, this molten mixture was compression molded to give a spherical molding of a diameter of 4 cm and a weight of 31 g. This molding was placed in a toilet bowl for men and washed with 7 liters of water at 3 hour intervals. This was repeatedly continued until it was drained out or disappeared. The results obtained are shown in Table 2.

The diminution in size of this molding became vigorous (more rapid) from the time when a size of a diameter of 2.5 cm and a weight of 6 g was reached. The size when this condition is reached is hereinafter referred to as the size "when the collapse becomes vigorous". At a size of a diameter of 1.5 cm and a weight of 1.8 g, the molding collapsed and disappeared.

EXAMPLES 3 AND 4

The procedure of Example 2 was repeated with the exception that a mixture of 50% by weight of adamantane and 50% by weight of TMN or a mixture of 40% by weight of adamantane and 60% by weight of TMN was used in place of the mixture of 30% by weight of adamantane and 70% by weight of TMN. The results obtained are shown in Tables 2 and 3.

TABLE 2

| TMN Content (wt %) | Processing Days | | | | | | |
|---|---|---|---|---|---|---|---|
| | 0 | 10 | 20 | 30 | 40 | 50 | 60 |
| 0 | 31 | 26.5 | 22 | 18 | 14.5 | 12 | 9 |
| 50 | 31 | 22.5 | 15 | 9.5 | 6 | 3 | 1.3 |
| 60 | 31 | 19.7 | 12 | 6.5 | 3 | 1 | — |
| 70 | 31 | 17.2 | 9.5 | 4.5 | — | — | — |
| 100 | 31 | 10 | 2.2 | — | — | — | — |

In Table 2, the values indicate the weight (grams) of the samples.

TABLE 3

| TMN Content (wt %) | Size at the time when the collapse became vigorous. | | Size at the time when the mold collapsed. | |
|---|---|---|---|---|
| | Diameter (cm) | Weight (g) | Diameter (cm) | Weight (g) |
| 50 | 1.0 | 1 | 0.5 | 0.1 |
| 60 | 1.4 | 1.2 | 0.8 | 0.2 |

EXAMPLE 5

To 100 parts by weight of a mixture of 30% by weight of adamantane and 70% by weight of TMN was added 2 parts by weight of geraniol as a perfume. This mixture was melted and uniformly mixed. After cooling, this molten mixture was compression molded to give a spherical molding of a diameter of 4 cm and a weight of 31 g.

EXAMPLE 6

The procedure of Example 5 was repeated with the exception that linalool was used in place of geraniol, whereby a molding was obtained.

EXAMPLE 7

Figure 1:
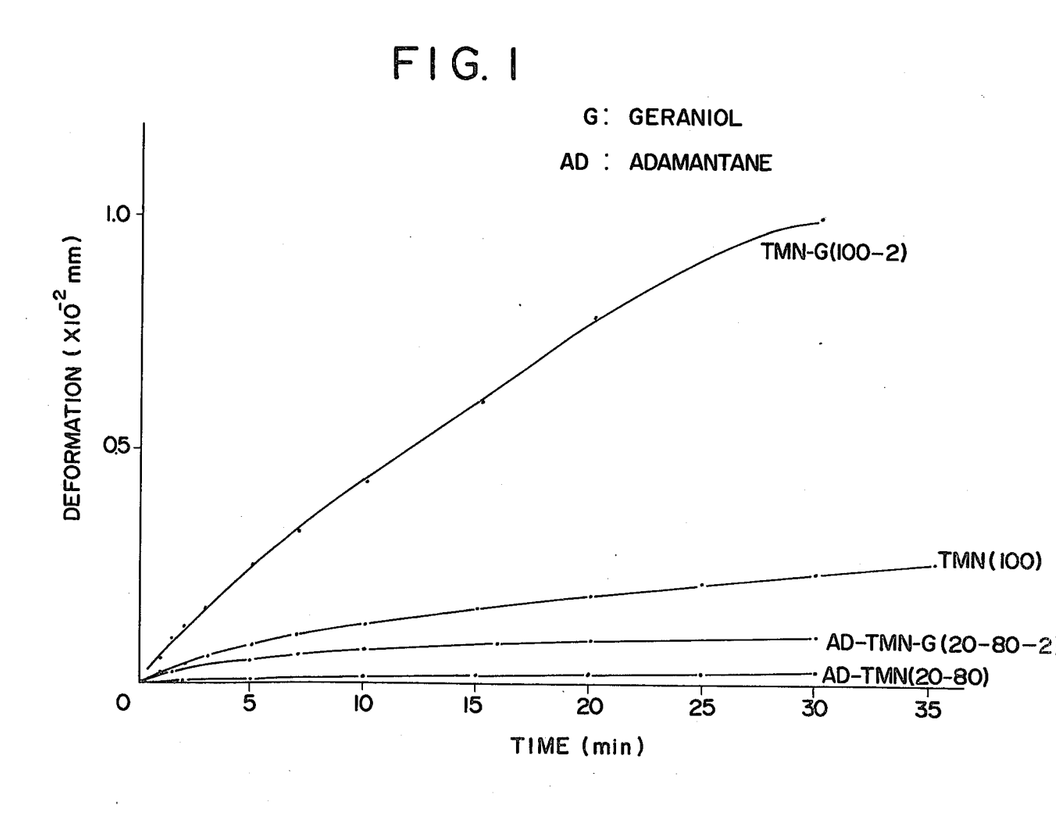
FIGS. 1 and 2 are graphs showing respectively the creep characteristics and the sublimation characteristics of a composition according to this invention.

A mixture of 20 parts by weight of adamantane and 80 parts by weight of TMN was melted by heating and uniformly mixed. This molten mixture was solidified by cooling and pulverized. This powder in the amount of 0.5 g was weighed out and compression molded at a pressure of 10 Kg/cm$^2$ to give a tablet of a diameter of 13.0 mm and a height of about 5 mm. This tablet was subjected to a creep test at a load of 2 Kg. The results obtained are shown in FIG. 1.

COMPARATIVE EXAMPLE 1

The procedure of Example 7 was repeated wherein only 0.5 g of TMN was used. The results obtained are shown in FIG. 1.

EXAMPLE 8

The procedure of Example 7 was repeated with the exception that 2 parts of geraniol was added to the mixture of 20 parts by weight of adamantane and 80 parts by weight of TMN. The results obtained are shown in FIG. 1.

COMPARATIVE EXAMPLE 2

The procedure of Example 8 was repeated with the exception that no adamantane was used. The results obtained are shown in FIG. 1.

EXAMPLE 9

A mixture of 20 parts by weight of adamantane and 80 parts by weight of TMN was melted by heating and uniformly mixed. To this mixture was added 1 part by weight of a perfume. The resulting mixture was immediately solidified by cooling and pulverized. This powder in the amount of 0.5 g was weighed out and compression molded to form a tablet of a diameter of 12.0 mm and a height of about 5 mm. The thus obtained tablet was sublimated in a stream of air at room temperature. The perfume content at which the weight of the tablet was ½ of the original weight, was measured. The results obtained are shown in Table 4. The perfume content is indicated as a relative content when the initial content after molding is set as 1.0.

COMPARATIVE EXAMPLE 3

The procedure of Example 9 was repeated with the exception that only 0.5 g of adamantane was used. The results obtained are shown in Table 4.

TABLE 4

| Perfume | Carrier | |
|---|---|---|
| | Adamantane-TMN | Adamantane |
| α-Ionone | 0.49 | 0.21 |

TABLE 4-continued

| Perfume | Carrier | |
|---|---|---|
| | Adamantane-TMN | Adamantane |
| Borneol | 0.92 | 0.33 |
| Cumarin | 1.20 | 1.12 |
| Nerolin | 1.03 | 0.41 |
| Linalool | 0.80 | 0.62 |

EXAMPLE 10

A mixture of 20 parts by weight of adamantane and 80 parts by weight of TMN was melted by heating and uniformly mixed. To this molten mixture was added 2 parts by weight of borneol. The resulting mixture was immediately solidified by cooling and pulverized. This powder in the amount of 37 g was compression molded at a pressure of 20 Kg/cm$^2$ to give a spherical sublimable molding of a diameter of 40 mm.

Figure 2:
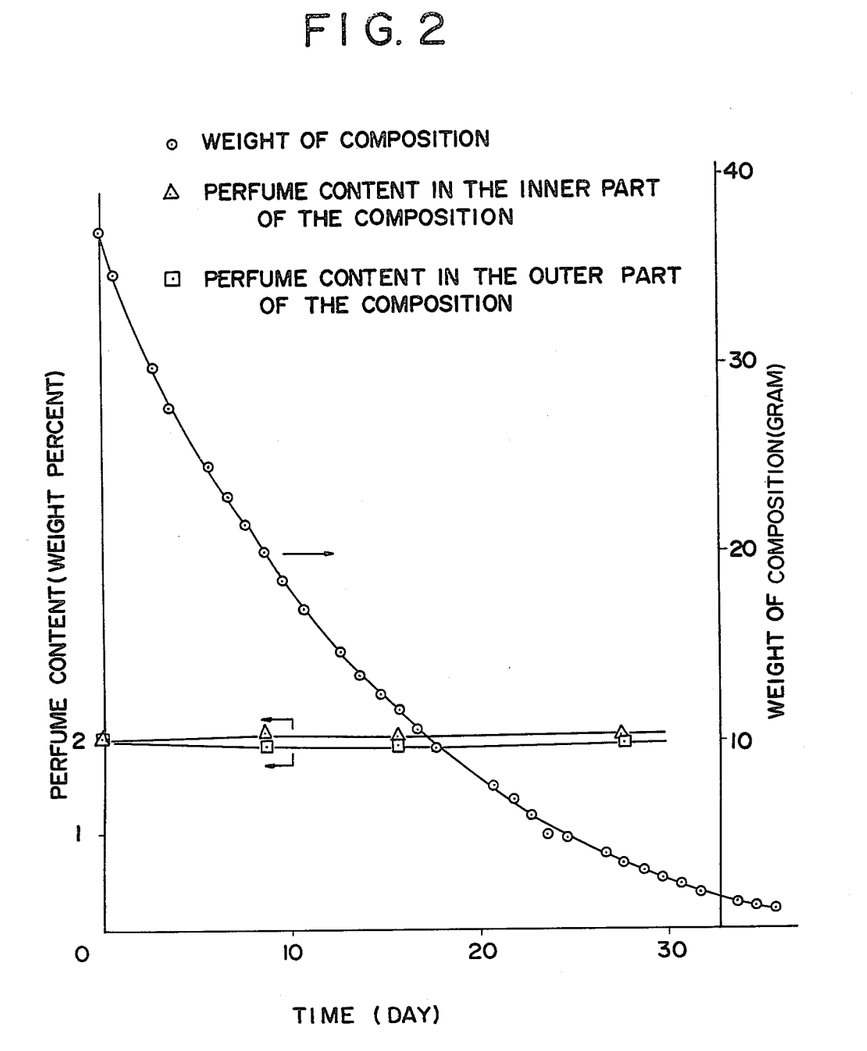

This spherical molding was sublimated in a stream of air at room temperature, and the sublimation characteristics of the perfume and carrier were measured. The results obtained are shown in FIG. 2. From FIG. 2, it can be seen that the perfume content is constant in spite of a decrease in the weight of the carrier. With other perfumes such as camphor, nerolin and the like, the same results were obtained.

EXAMPLE 11

Figure 3:
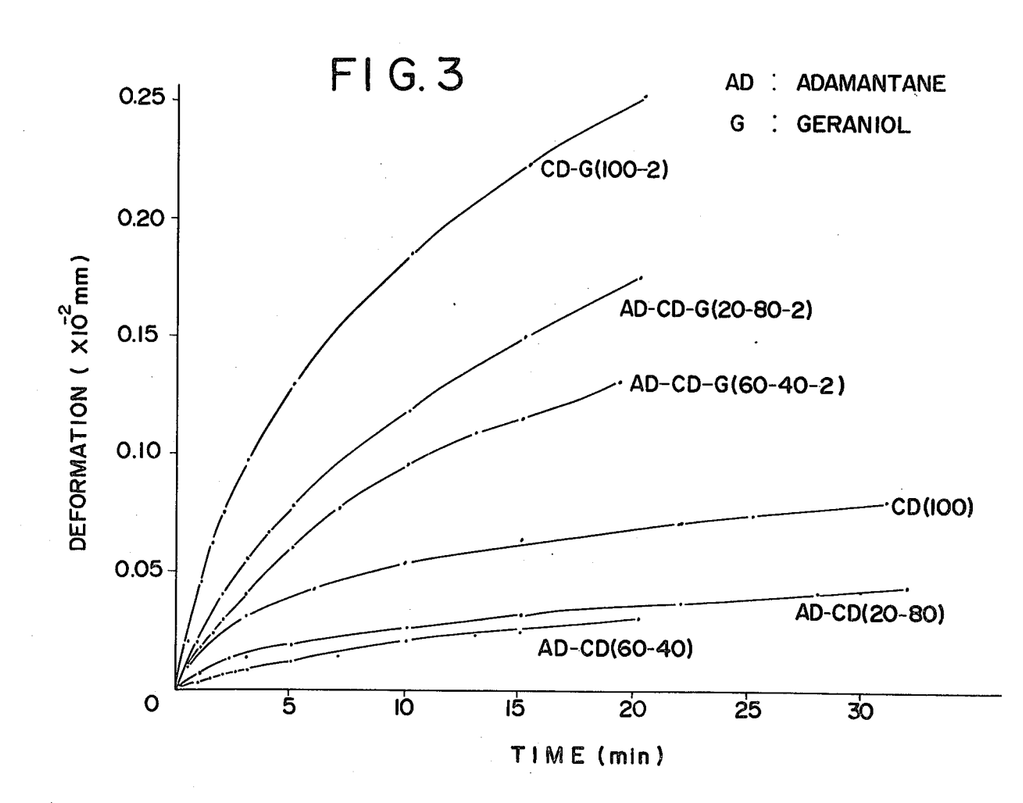
FIG. 3 is a graph showing the creep characteristics of a composition according to this invention.

A mixture of 60 parts by weight of adamantane and 40 parts by weight of CD was melted by heating and uniformly mixed. To this molten mixture was added 2 parts by weight of geraniol. The resulting mixture was solidified by cooling and pulverized. This powder in the amount of 0.5 g was compression molded at a pressure of 10 Kg/cm$^2$ to give a tablet of a diameter of 13.0 mm and a height of about 5 mm. This tablet was subjected to a creep test at a load of 20 Kg. The results obtained are shown in FIG. 3.

EXAMPLE 12

The procedure of Example 11 was repeated with the exception that no geraniol was used. The results obtained are shown in FIG. 3.

EXAMPLE 13

The procedure of Example 11 was repeated wherein a mixture of 20 parts by weight of adamantane, 80 parts by weight of CD and 2 parts by weight of geraniol was used. The results obtained are shown in FIG. 3.

EXAMPLE 14

The procedure of Example 13 was repeated with the exception that no geraniol was added. The results obtained are shown in FIG. 3.

COMPARATIVE EXAMPLES 4 AND 5

The procedure of Example 11 was repeated wherein CD alone or a mixture of 100 parts by weight of CD and 2 parts by weight of geraniol was used. The results obtained are shown in FIG. 3.

EXAMPLE 15

A mixture of adamantane and CD in the amount of 100 parts by weight was dissolved in pentane. To this solution was added 2 parts by weight of geraniol. Thereafter, the geraniol was distilled away. The thus obtained powder in the amount of 0.5 g was compression molded at a pressure of 10 Kg/cm² to give a tablet of a diameter of 13.0 mm and a height of about 5 mm.

Figure 4:
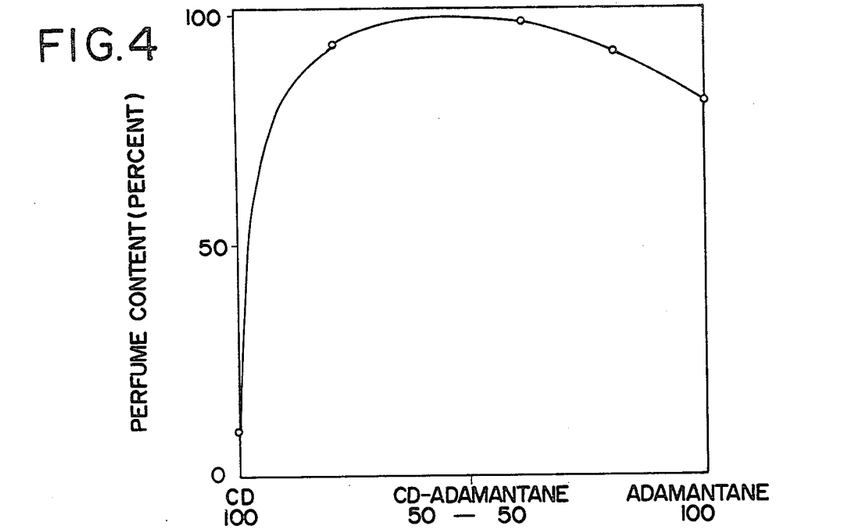
FIGS. 4 and 5 are graphs showing respectively the perfume content and the perfume retention ratio.

With the perfume content of the powder after the distillation of pentane is set as 100, the perfume content of the tablet after molding was measured. The results obtained are shown in FIG. 4.

EXAMPLE 16

Figure 5:
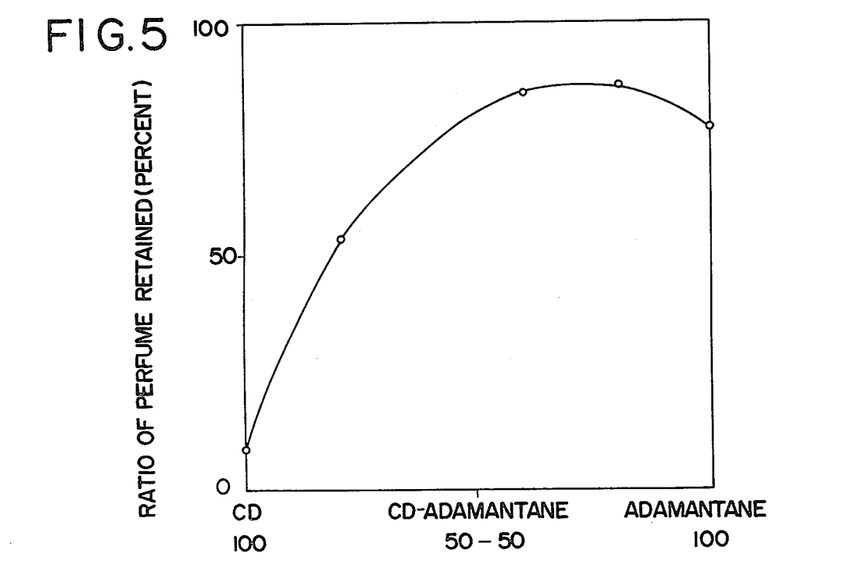

The tablet obtained in Example 15 was sublimated in a stream of air at room temperature. The perfume content at the time when 20% of the weight of the tablet was sublimated, was measured. This is indicated when the initial content is set as 100. The results obtained are shown in FIG. 5.

EXAMPLE 17

A uniform molten mixture of 20 parts by weight of adamantane, 80 parts by weight of TMN and 3 parts by weight of a moth-proofing agent was poured into a tablet forming apparatus having a diameter of 20 mm and a thickness of 10 mm to form a tablet of a weight of 2.3 g. For comparison, a tablet containing no moth-proofing agent was molded.

With the thus obtained tablet, the moth-proofing test thereof against insects for clothes was conducted. As the insect, larvae of clothes moth were used (cultured on a powder of dried bonito containing 20% of dry yeast powder in a thermostat chamber of 20° C. and 65% RH: 50-days old after hatching; average weight 38.7 mg/10 larvae). In a box formed of a transparent plastics (340 mm ×230 mm× 60 mm (depth)), two sets of two-ply sheep blanket were placed with an interval of 250 mm therebetween. One of them was tested while the other as a standard. Two tablets prepared above were placed between them. Twenty larvae were placed in the central portion of the box, and a 40 mesh wire net was provided on the box. The test was conducted at 30° C. in a room. The testing period was 21 days and five tests were averaged.

The moth-proofing effect was determined by measuring the amount of the blanket eaten by the larvae and calculating a moth-proofing index by the following equation. The results obtained are shown in Table 5.

$$\text{Moth-proofing Index} = \frac{(S - T)}{(S + T)} \times 100$$

S = Amount of Standard Sheep Blanket eaten by Larvea

T = Amount of Test Sheep Blanket eaten by Larvea

For example, in such a case that the examination of moth-proofing agent was carried out using a tablet containing linalool, each value of S and T was 21.4 mg and 0.2 mg respectively. On the other hand, in the case of a tablet containing no moth-proofing agent, each value of S and T was 17.7 mg and 6.8 mg respectively.

TABLE 5

| Moth-proofing Agents | Moth-proofing Index |
|---|---|
| Linalool | 98.2 |
| Thymol | 99.1 |
| Carrier alone | 44.5 |

EXAMPLE 18

An uniform molten mixture of 10 parts by weight of adamantane, 90 parts by weight of TMN and 3 parts by weight of a rust-preventing agent was poured into a tablet forming apparatus having a diameter of 20 mm and a thickness of 10 mm to form a tablet of a weight of 2.3 g. For comparison, a tablet containing no rust-preventing agent was molded.

The rust-preventing effect was measured according to JIS ZO236-1974 (General testing method of rust-preventing oil) 6.7 Vaporizable rust-preventing properties. The results obtained are shown in Table 6.

TABLE 6

| Rust-preventing Agent | Formation of Rust |
|---|---|
| Morpholine | No |
| Diisopropylamine | No |
| Dicyclohexylamine | No |
| Carrier alone | Formed |

JIS ZO236-1974, 6.7 Vaporizable rust-preventing properties 6.7.1 Test Piece

Carbon steel S15C prescribed in JIS G 4051 (Carbon Steel for Machine Structural Use) is cut to a desired size. At the central portion of one end of the test piece is provided a blind hole having a flat bottom. The other end is smoothly abrade until there is no scratch, and it is then cleaned with warm petroleum naphtha and warm anhydrous methanol in this order.

6.7.2 Construction of Test Piece

The end of the test piece where the blind hole is provided, is inserted in a rubber stopper with a hole provided in the central portion thereof. On the other hand, an aluminum tube is passed through a rubber stopper for use in an one liter wide-mouthed bottle prescribed in JIS R3503 (Glass Apparatus for Chemical Analysis) at the central portion thereof in such a manner that the both ends extend from the rubber stopper in the same length. One end of the aluminum tube is inserted into the hole of the rubber stopper in which the test piece has been inserted, until it reaches the test piece. Before pluging the 1 liter wide-mouthed bottle, two tablets are placed therein. In addition, 10 ml of a glycerin aqueous solution having a specific gravity of 1.077 at 20° C. is charged to a glass cell and the glass cell is placed on the bottom of the bottle.

6.7.3 Operation

The test piece is stored at a temperature of 20±2° C. for 20 hours. Then, cold water at 2.0±0.5° C. is poured in the aluminum tube until it is filled therewith. After 3 hours, the water is removed, and the formation of rust at the abraded portion of the test piece is examined with a 5 or more magnification microscope. This test is conducted on 3 test pieces. At the same time, a blank test is conducted. If no rust is formed on a test piece of the blank test, the test is repeated.

EXAMPLE 19

A mixture of 20 parts by weight of adamantane and 80 parts by weight of TMN was melted by heating and uniformly mixed in a stream of nitrogen. Then, 2 parts by weight of citral and 0.1 part by weight of hydroquinone monomethyl ether as an antioxidant were added thereto. The resulting mixture was poured into a mold for production of a spherical molding of a diameter of 40 mm to form a sublimable molding of a weight of about 30 g.

In order to obtain the volatility characteristics of the molding, the molding was sublimated in a stream of air at room temperature. After a lapse of 21 days, the results were obtained. The results obtained are shown in Table 7. For comparison, a molding where no antioxidant was used, was tested, and the results obtained are also shown in Table 7.

TABLE 7

| Antioxidant | Weight of Sample (g) | Concentration of Citral (%) | Weight of Toluene — insoluble Material (mg) |
| --- | --- | --- | --- |
| Added | 3.6 | 1.2 | 4 |
| No added | 4.0 | 0.2 | 153 |

EXAMPLE 20

A mixture of 20 parts by weight of adamantane and 80 parts by weight of TMN was melted by heating and uniformly mixed. The resulting solution was poured in a mold for production of a spherical molding of a diameter of 40 mm to form a spherical sublimable molding of a weight of 30 g.

The thus obtained spherical molding was divided into two parts along the equator thereof. From the surface portion of the equator and the core portion thereof, test samples were taken out in the amount of 0.5 g. With these samples, the concentration distribution of adamantane was measured. The results obtained are shown in Table 8. The average value was the value obtained by dissolving the spherical molding in toluene and measuring the concentration of adamantane.

COMPARATIVE EXAMPLE 6

A mixture of 20 parts by weight of adamantane and 80 parts by weight of TMN was melted by heating and uniformly mixed. This molten mixture was immediately solidified by cooling and pulverized. This powder was compression molded at a molding pressure of 20 Kg/cm$^2$ and a spherical molding of a diameter of 40 mm was obtained. With this molding, the concentration distribution of adamantane was measured in the same manner as in Example 20. The results obtained are shown in Table 8.

TABLE 8

|  | Melt Molding (%) | Compression Molding (%) |
| --- | --- | --- |
| Surface portion | 22 | 20 |
| Core portion | 15 | 20 |
| Average value | 20 | 20 |

EXAMPLE 21

A mixture of 20 parts by weight of adamantane and 80 parts by weight of TMN was melted by heating and uniformly mixed. To this molten mixture was added 1 part by weight of linalool as a perfume. The thus obtained solution was poured into a mold for production of a spherical molding of a diameter of 40 mm to form a spherical sublimable molding of a weight of 30 g.

The molding so obtained was subjected to the same procedure as in Example 20; i.e., samples were taken out form the same portions as in Example 20 and the concentration of linalool at each portion was measured. The results obtained are shown in Table 9. The average value was measured by dissolving the molding in toluene and measuring the concentration of linalool.

EXAMPLE 22

The procedure of Example 21 was repeated with the exception that the amount of linalool added was changed to 2 parts by weight. The results obtained are shown in Table 9.

COMPARATIVE EXAMPLE 7

The compositions used in Examples 21 and 22 were compression molded at a molding pressure of 20 Kg/cm$^2$. With the thus obtained spherical sublimable molding, the concentration of linalool was measured in the same manner as in Example 21. The results obtained are shown in Table 9.

TABLE 9

|  | 1 part by weight | | 2 parts by weight | |
| --- | --- | --- | --- | --- |
|  | Melt Molding | Compression Molding | Melt Molding | Compression Molding |
| Surface Portion | 0.93 | 0.86 | 1.78 | 1.01 |
| Core Portion | 1.52 | 0.85 | 3.35 | 0.92 |
| Average Value | 1.03 | 0.86 | 2.07 | 0.98 |

EXAMPLE 23

A mixture of 20 parts by weight of adamantane and 80 parts by weight of naphthalene was melted by heating and uniformly mixed. To this mixture was added 1 part by weight of linalool. The resulting solution was poured into a mold for production of a spherical molding of a diameter to form a spherical sublimable molding of a weight of about 30 g.

With the thus obtained spherical molding, the concentration distributions of adamantane and linalool were measured in the same manner as in Example 20. With adamantane, the core portion was 94 per 100 of the surface portion, whereas with linalool, the core portion was 100 per 16 of the surface portion. In indicating the concentration distribution, the higher concentration of linalool in either the surface portion or the core portion is indicated as 100, and the concentration of the other is given as a relative value.

COMPARATIVE EXAMPLE 8

A mixture of 20 parts by weight of adamantane and 80 parts by weight of TMN was melted by heating and uniformly mixed. To this mixture was added 3.5 parts by weight of linalool. The resulting solution was cooled rapidly and pulverized.

This powder in the amount of 0.5 g was weighed out and compression molded to form a tablet of a diameter of 13.0 mm and a height of about 5 mm. In this compression molding, molding pressures of 5, 10, 20 and 30 Kg/cm$^2$G were employed. In each sample, the concentration of linalool (weight of linalool/weight of tablet × 100) was measured.

The amount of linalool added was changed to 10 parts by weight and the influence of molding pressure was measured in the same manner as above. The results obtained are shown in Table 10. The concentration of linalool in a tablet prepared by melt molding of the same mixture was 3.3% when 3.5 parts by weight of linalool was added, and 9.0% when 10 parts by weight of linalool was added respectively.

TABLE 10

|  | Amount of Linalool added | |
| --- | --- | --- |
| Molding Pressure (Kg/cm$^2$G) | 3.5 parts by weight (%) | 10 parts by weight (%) |
| 5 | 1.3 | 1.5 |
| 10 | 1.2 | 1.4 |
| 20 | 1.2 | 1.2 |

TABLE 10-continued

| Molding Pressure (Kg/cm$^2$G) | Amount of Linalool added | |
|---|---|---|
| | 3.5 parts by weight (%) | 10 parts by weight (%) |
| 30 | 1.2 | 1.3 |

EXAMPLE 24

Figure 6:
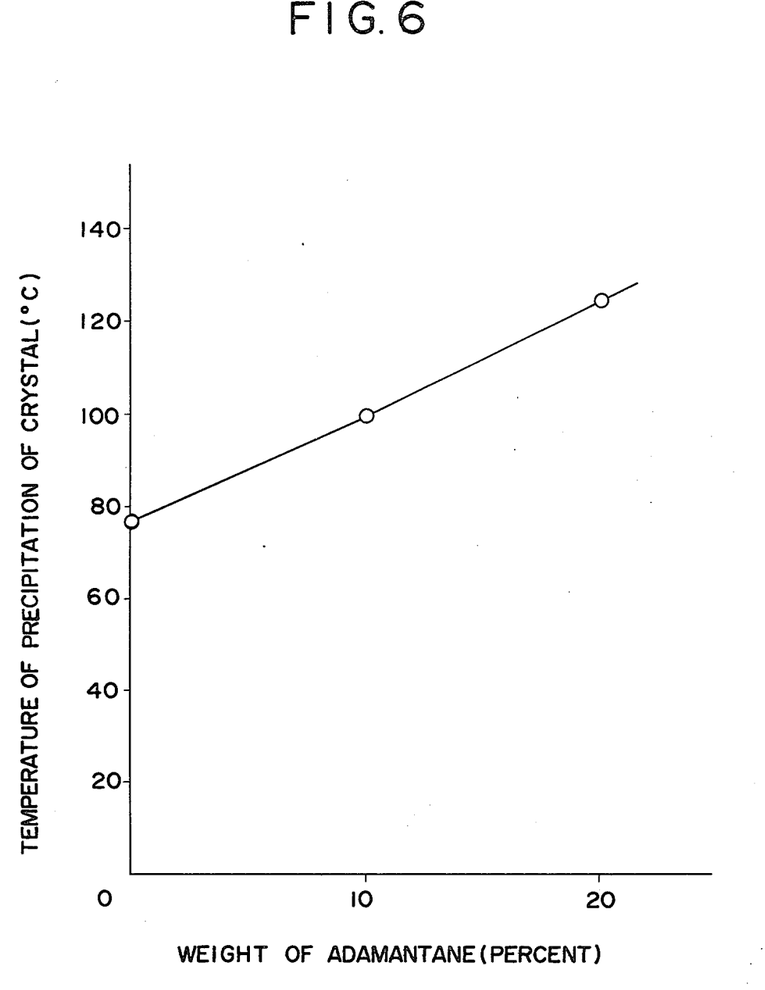
FIG. 6 is a graph showing a relation between the concentration of adamantane and the crystal precipitating temperature of an adamantane-TMN system.

A mixture of TMN and adamantane was melted. The resulting solution was cooled with a heat transfer medium at various temperatures, and the temperature at which the crystallization began, was measured. The results obtained are shown in FIG. 6.

EXAMPLE 25

A mixture of 20 parts by weight of adamantane, 80 parts by weight of TMN and 4 parts by weight of linalool was melted by heating, poured into a mold and solidified by cooling to form a disk-like molding of a diameter of 42 mm and a height of 8.2 mm.

Figure 9:
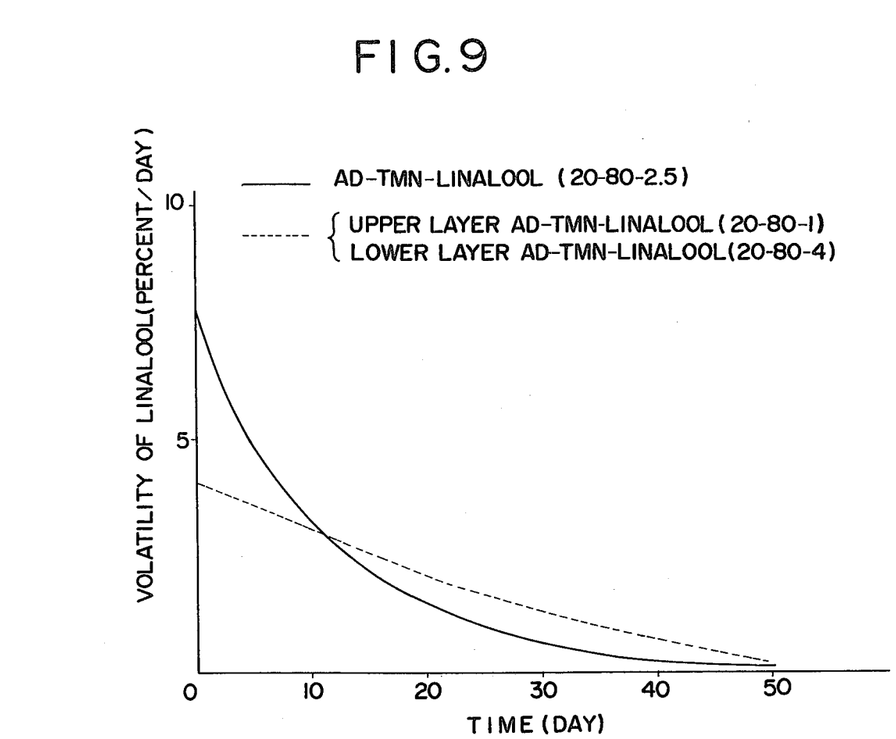
FIG. 9 indicates a change with time in the evaporation ratio of linalool.

Then, a mixture of 20 parts by weight of adamantane, 80 parts by weight of TMN and 1 part by weight of linalool was melted by heating, poured on the surface of the above prepared disk-like mold to give a molding of a diameter of 42 mm and a height of 16.4 mm. A change with time in the volatilization ratio of the linalool contained in the laminated disk-like molding was measured and the results obtained are shown in FIG. 9.

In the same manner as above, a mixture of 20 parts by weight of adamantane, 80 parts by weight of TMN and 2.5 parts by weight of linalool was melted by heating, poured into a mold and solidified by cooling to form a single layer disk-like molding of a diameter of 42 mm and a height of 16.4 mm. With this single layer disk-like molding, a change with time in the volatilization ratio of the linalool contained in the single layer disk-like molding was measured and the results obtained are shown in FIG. 9.

In measuring the volatilization ratio, the molding was first sublimated from the surface of the upper layer in a stream of air at room temperature and a change in the weight of the molding was measured. Then the vaporization ratio was calculated from the graph which showed the relation between the change in the weight of the molding and a change with time in the content of linalool. In FIG. 9, the area of the part surrounded by the curve, abscissa and ordinate corresponds to 100%. From FIG. 9, it can be seen that with the above laminated molding, the volatilization ratio was 2 to 6% per day by 20 days from the beginning of the sublimation and that the volatilization ratio was maintained at a substantially constant level.

What is claimed is:

1. A process for producing a sublimable molded article which comprises melt-molding a composition comprising (i) adamantane and (ii) at least one compound selected from the group consisting of endo-trimethylenenorbornane and cyclododecane.

2. The process of claim 1, wherein said composition also contains an effective component which is at least one compound selected from the group consisting of α-ionone, borneol, camphor, linalool, geraniol, cumarin, nerolin, citronillol, morpholine, thymol, dicyclohexylamine and diisopropylamine.

3. The process of claim 2, wherein said composition comprises adamantane and endo-trimethyleneorbornane.

4. The process of claim 3, wherein said composition comprises 1 to 10 parts by weight of adamantane to 99 to 90 parts by weight of endo-trimethylenenorbornane.

5. The process of claim 3, wherein said composition comprises 10 to 25 parts by weight of adamantane to 90 to 75 parts by weight of endo-trimethylenenorbornane.

6. The process of claim 3, wherein said composition comprises 25 to 60 parts by weight of adamantane to 75 to 40 parts by weight of endo-trimethylenenorbornane.

7. The process of claim 2, wherein said composition comprises adamantane and cyclododecane.

8. The process of claim 7, wherein said composition comprises 10 to 50 parts by weight of adamantane to 90 to 50 parts of cyclododecane.

9. A sublimable multi-layer molded article comprising (i) adamantane; (ii) at least one compound selected from the group consisting of endo-trimethylenenorbornane and cyclododecane; and (iii) an effective component which is at least one compound selected from the group consisting of α-ionone, borneol, camphor, linalool, geraniol, cumarin, nerolin, citronillol, morpholine, thymol, dicyclohexylamine and diisopropylamine, wherein the ratio of the effective component contained in each layer is successively increased from the outer layer to the inside or inner layer.

10. The molded article of claim 9, comprising (i) adamantane and (ii) endo-trimethylenenorbornane.

11. The molded article of claim 9, comprising (i) adamantane and (ii) cyclododecane.

* * * * *